Figure 1:
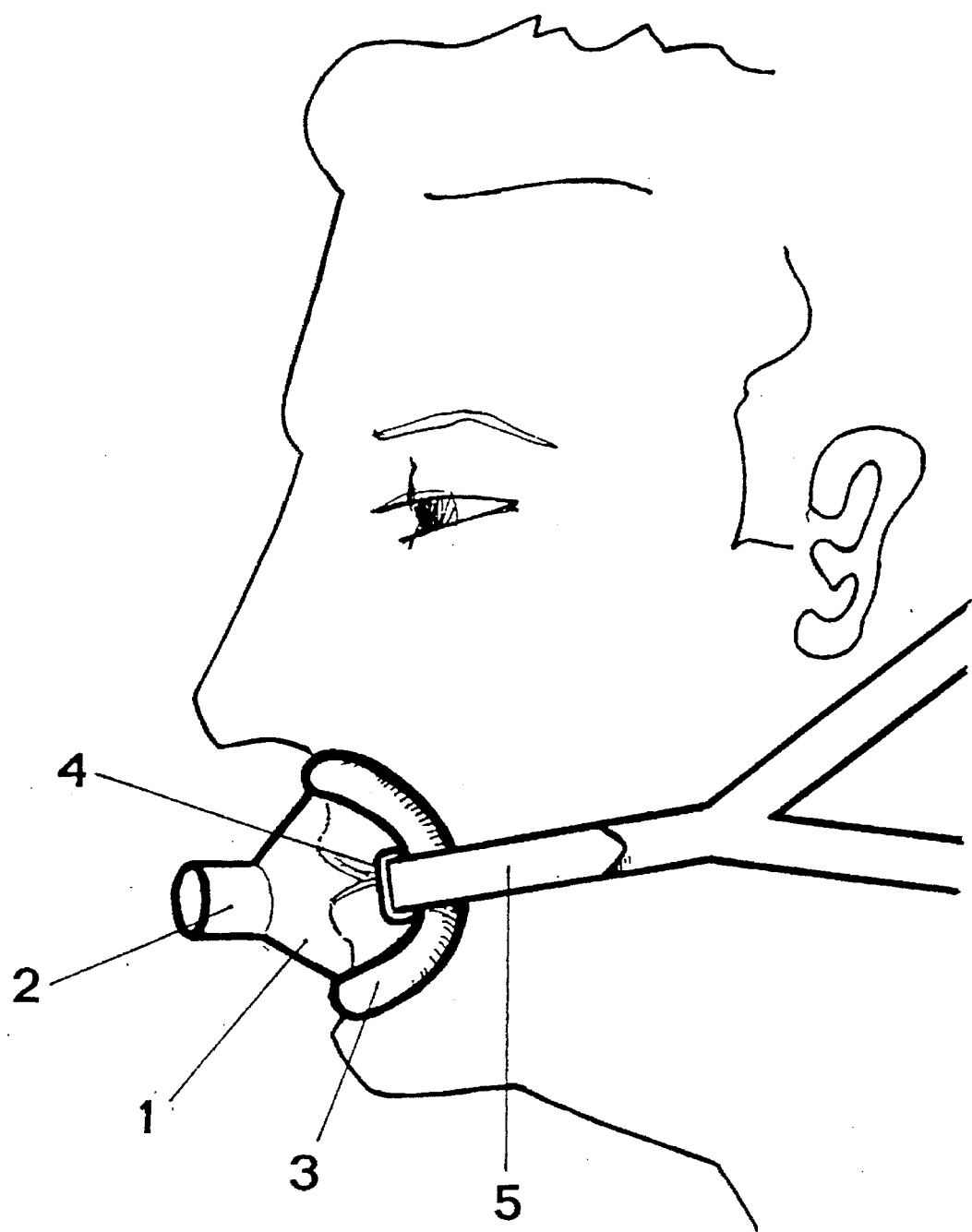

United States Patent [19]
Jacobelli

[11] Patent Number: 5,660,174
[45] Date of Patent: Aug. 26, 1997

[54] BUCCAL RESPIRATION MASK

[76] Inventor: Chantal Jacobelli, 27 Rue Maréchal Foch, 45000 Orleans, France

[21] Appl. No.: 581,566

[22] PCT Filed: Jul. 13, 1994

[86] PCT No.: PCT/FR94/00879

§ 371 Date: Jan. 16, 1996

§ 102(e) Date: Jan. 16, 1996

[87] PCT Pub. No.: WO95/02428

PCT Pub. Date: Jan. 26, 1995

[30] Foreign Application Priority Data

Jul. 13, 1993 [FR] France .................................. 93 08850

[51] Int. Cl.⁶ .................................................. A61M 16/00
[52] U.S. Cl. .................................. 128/206.24; 128/206.21
[58] Field of Search ........................... 128/206.11, 206.12, 128/206.13, 206.14, 206.15, 206.16, 206.17, 206.18, 206.19, 206.21, 206.22, 206.23, 206.24, 206.25, 206.26, 206.27, 206.28, 207.11

[56] References Cited

U.S. PATENT DOCUMENTS

| 4,274,406 | 6/1981 | Bartholomew | 128/206.21 |
| 4,449,526 | 5/1984 | Elam | 128/206.21 |
| 5,069,205 | 12/1991 | Urso | 128/206.21 |

*Primary Examiner*—Vincent Millin
*Assistant Examiner*—Robert N. Wieland
*Attorney, Agent, or Firm*—Harris Beach & Wilcox, LLP

[57] ABSTRACT

A buccal respiratory mask includes a shell which has an adaptor for connecting to a respirator tube and a seal which is applied against an area surrounding a patient's mouth. The mask may include a tab or a lug for securing a fastening strap that secures the mask to the patient's face. The mask of the invention is generally used for non-invasive mechanical ventilation of patients suffering from transient respiratory failure.

8 Claims, 5 Drawing Sheets

BUCCAL RESPIRATION MASK

The present invention concerns a buccal respiratory mask.

The use of respiratory mask for non-invasive ventilation is more and more frequent. The most usual indication is the mechanic ventilation of patients suffering from transient respiratory failure, as for example, post-surgery intensive care or acute failure of chronic respiratory deficiency. This method provides an alternative to invasive methods of artificial ventilation with endotracheal tube (related with many complications).

Respiratory masks now proposed, which are either nasal or naso-buccal (facial mask), do not give full satisfaction.

In fact, one of the main problem related to non-invasive ventilation with mask, is to ensure a perfect air-tightness between the mask and the patient's face. So that the gas propulsed by the respirator can reach entirely the lungs of the patient.

Gas losses are unfortuntely frequent because respiratory therapy involves sometimes great positive pressure (it may reach 35 cm of water), and because the masks have to fit with any faces of the patients. When they occur, these gas losses are deleterious because the patient does not receive the necessary gas volume for his treatment. In addition, due to the face shape, these gas losses occur generally at the nose's roots, the gas escaping in the eyes, which may lead to conjunctivitis and interruption of the ventilation by mask.

In order to prevent these gas losses, in spite of the presence of seal made of different kinds of materials (flexible membranes, foam, inflated structures . . . ), the therapist has often to exert on the fastening means (harness, strap . . . ) a great tension. This tension leads to trauma of the compression points (especially the root of the nose, but also the suborbital area) which is prejudicial to the patient's comfort and prohibits a long use of mask if important cutaneaous injuries which may lead to necessary stop the ventilation by mask are avoided.

In addition, an other drawback of the nasal or naso-buccal masks is that they present a great inner volume because they have to enclose the nose. This leads to an important dead volume and so increases the amount breathed out gas which is re-inhaleted. For an adult naso-buccal mask, these volumes are comprised between 180 ml and 300 ml. For a child nasal mask,, these volumes are comprised between 100 ml and 150 ml.

There also exist a kind of buccal respiratory system consisting of a pipette connected to a respirator. These pipettes are used by patients who are conscious under artificial ventilation few hours a day (especially patients with chronic respiratory failure). A mouthpiece allows to secure a little bit one of these pipettes to the patient's face. But, for the following detailed reasons, this system is not fit for intensive care use. Its air-tightness is not sufficient for drowsy or agitated patients (inadequate fastening means, too important overhang, possibility for the agitated patients to easely push out the pipette with their teeth). In addition, in case of prolonged ventilation (in fact, it can take place 22 hours a day), the use of a pipette is not comfortable for the patients. Finally, in case of moderate regurgitation or expectoration, these are inhaleted by the patient (no space to put them, no way for the therapist to see them and to remove mouthpiece and the pipette to avoid their inhalation).

The present invention intends to overcome the disadvantages related to the different way of non-invasive ventilation, by means of a buccal respiratory mask.

In fact, contrary to received ideas, it has been found that buccal respiratory masks serve favourably as substitute for the different systems actually used for non-invasive ventilation.

Lighter, smaller, with a minimum inner volume (thus decreasing the dead volume and so the rebreathing) and provided with a better adequacy, the applying of a air-tightness buccal mask and its bearing on the patient's face are made easier.

The main disadvantages of the existing masks (nasal or naso-buccal) do not exist anymore; as a matter of fact, no more conjunctivitis related to the gas losses, no more cutaneous injuries on the nose's root and suborbital area may be seen.

In addition to the suppression of the disadvantages related to the use of the nasal and naso-buccal masks, the use of the buccal mask raises specific advantages, such as:

the possibility to place a naso-gastric tube during a non-invasive ventilation (which allows drugs or food administration, gastric drainage by aspiration or by trap);

the possibility to place a nasal tube for oxygen (preservation of the desirable FIO2 even in case of an inopportune removal of the mask);

the possibility to realise bronchic fibro-aspirations during non-invasive ventilation.

Figure 2:
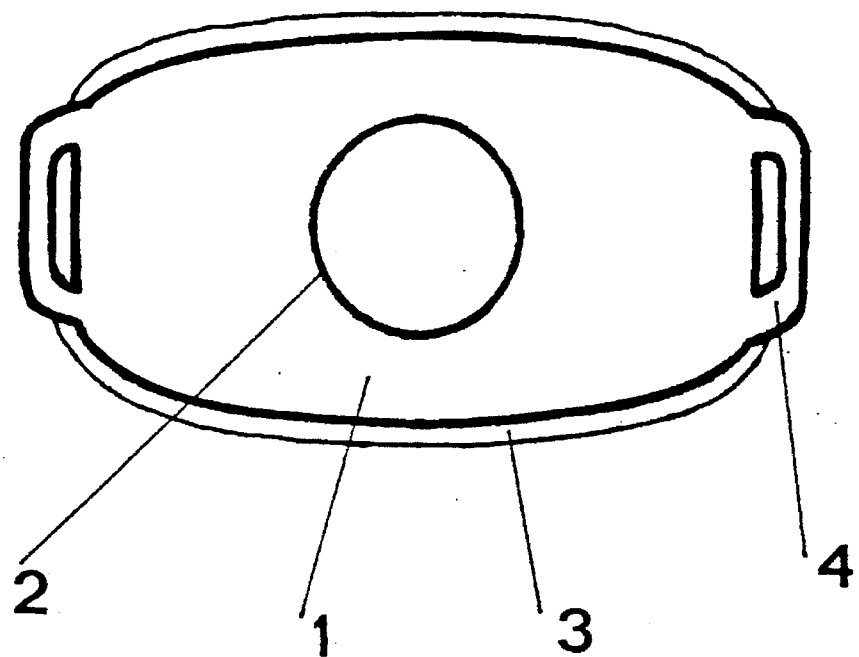
Figure 3:
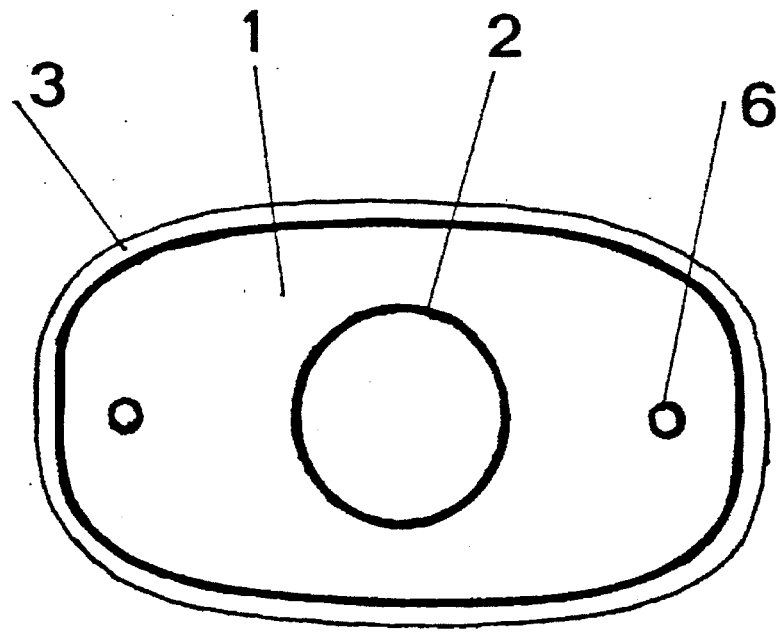

The mask of the present invention, intended to be used for mechanical non-invasive ventilation, constitutes the connexion between the patient's mouth and the inspiration-expiration tube issuing from the respirator. This mask (FIG. 1) comprises a shell (1), which can be, for example, an ovoid dome made of plastic. It is produced by injection, thermo-forming or any other appropriated means. The material used is preferably transparent (thus allowing the therapists to see the possible regurgitations or expectorations of the patient), and if possible, presents an elastic flexibility in order to slightly deform when applied on the patient's face. On this shell, facing the mouth, there is an adaptor (2), pivoting or not, for connection to a standard respirator tube. The antero-posterior distance of the shell is low, so as to reduce as far as possible the free cavity in front of the mouth. So, the dead volume is reduced. For the buccal mask of an adult of middle height, the dead volume is less than 100 ml (it can be greater for the mask of an adult of great height and much more smaller for the mask of an adult of small height). The mask's shell may comprise (FIG. 2 and FIG. 3), on each side of the patient's mouth and along its axis, a tab (4) or a lug (6), intended to secure a fastening strap (5) as described thereafter. The shell comprises on its periphery an airtightness seal (3). This seal applies around the mouth against the area between the nose and the upper lip, the lower lip and the chin, and against the area of the right and left cheeks lying outside the labial commissures.

If the mask is not made in one piece, the seal is then fixed to the shell by sticking, welding, ratchet or any appropriated means.

Figure 4:
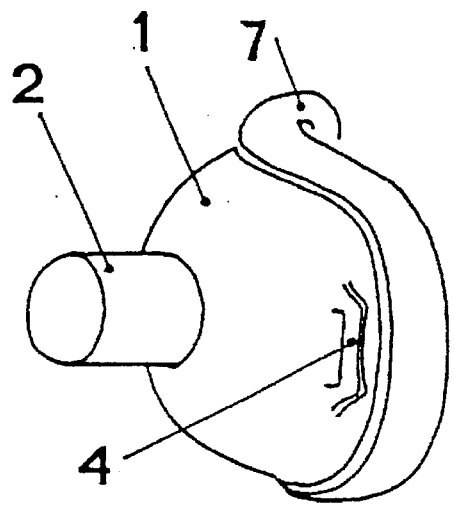
Figure 4:
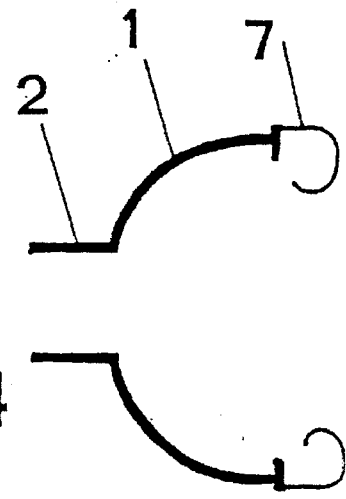
Figure 5:
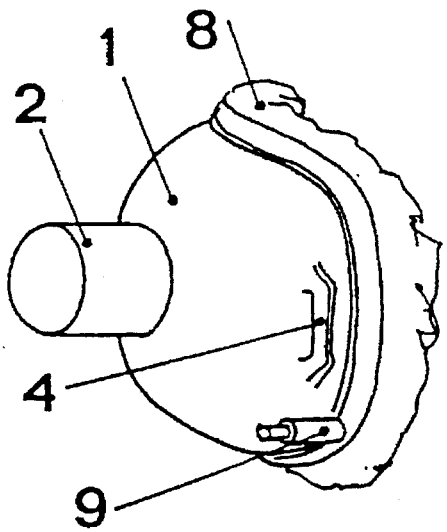
Figure 5:
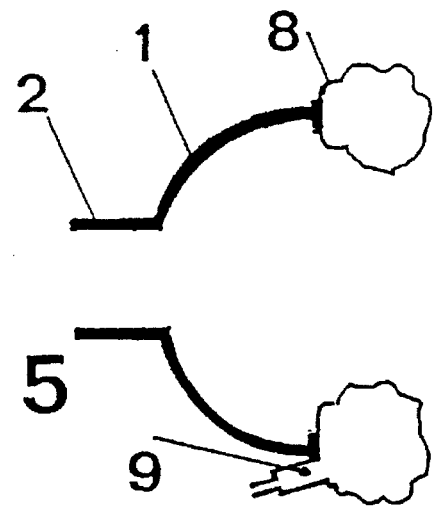
Figure 6:
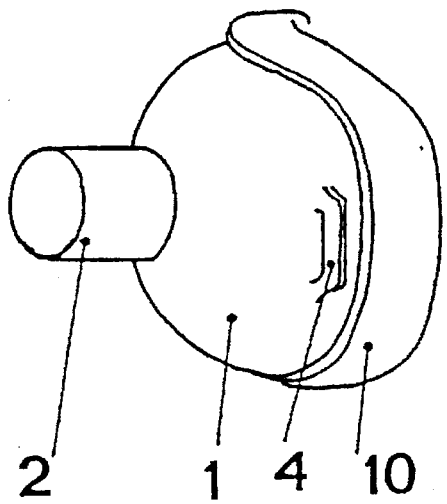
Figure 6:
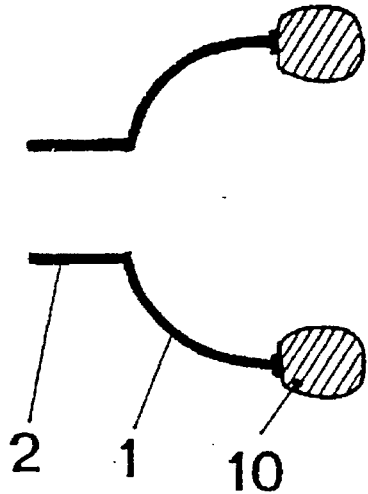

The seal consists (FIG. 4) of a sheet of plastic, rubber or silicone forming a pad (7) which can deform when the mask is applied on the patient's face, so as to ensure air-tightness. In an other embodiment (FIG. 5), this seal made of plastic, rubber or silicone for example, is an inflated cushion (8) with a valve (9) allowing the air inflation with a syringue. In another embodiment (FIG. 6), this seal is a foam or a sponge, covered or not with latex (10) slightly compressed when the mask is applied on the patient's face.

In another way of manufacture with an adequat material (silicone for example), the mask (shell, seal, adaptor . . . ) may be realised in one piece.

The materials used and the methods of assembling have an impact on the manufacture costs of the mask as to the possibility of cleaning, desinfection and sterilisation. Thus, as regard of the manufacture's technique and the materials used, the masks are either fit for many use, or fit for single use and so thrown away at the end of the patient's treatment.

During a non-invasive ventilation with a buccal mask, in some cases (hypotonic patient), at the time of insufflation, some gas losses may occur through the nostrils (the weak palate does not ensure air-tightness between the mouth and the nose). If such losses occur, it is enough to obturate the nostrils, either from outside (nose clip), or from inside (cotton-wool).

Figure 7:
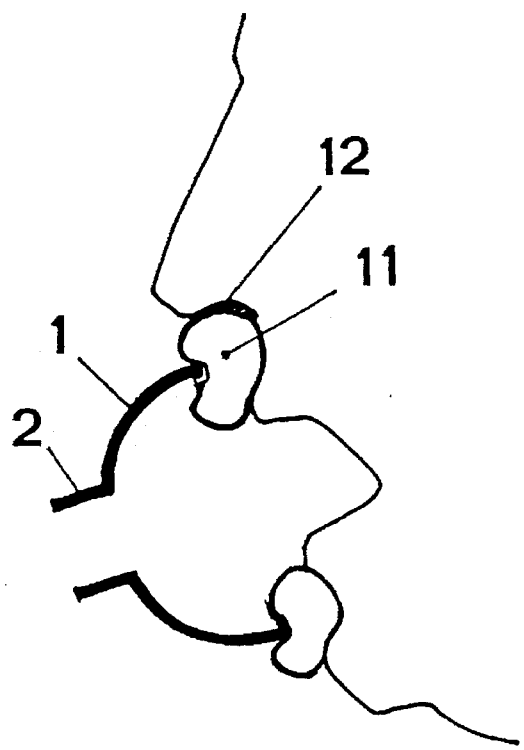

In order to avoid this phenomenon, a buccal mask with a specific embodiment can be used (FIG. 7). This buccal mask is characterized by the fact that its seal (for example, a inflated cushion) is large enough (11) while ensuring air-tightness with the mouth, to be able to deform, and then obturate with its upper part the patient's nostrils (12) in applying against them.

Figure 8:
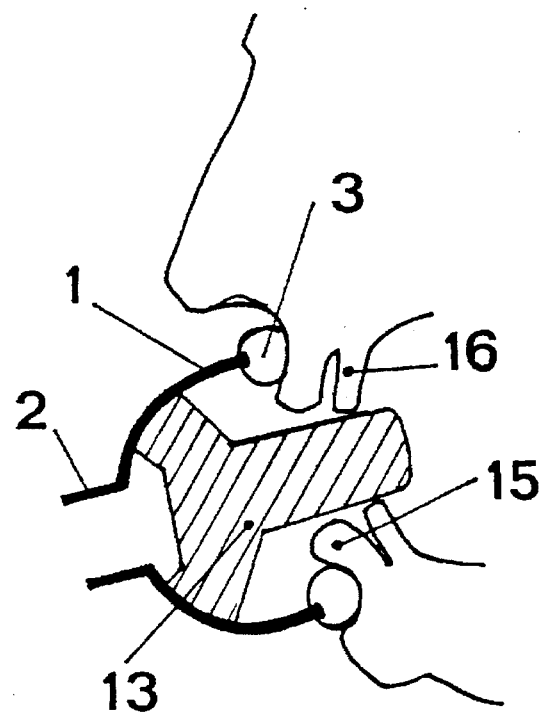
Figure 9:
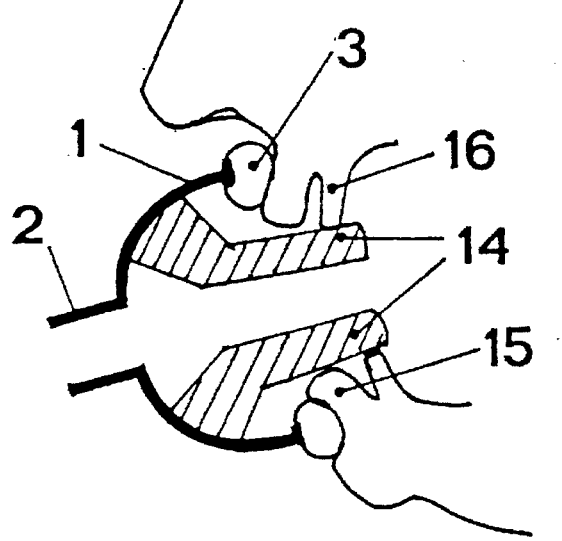

Other embodiments of buccal mask (FIG. 8 and FIG. 9) are characterized in that they have one or more mouth retractors. Being inside the mask, it is either a sagittal retractor (13), either two lateral retractors (14). Since they are realised by material wrinkles, these retractors embed themself between the patient's lips (15) or teeth (16), in order to warrant a good penetration of the gas in the patient's lungs.

The mask is held on the patient's face by a fastening trap with laces or straps. One can use classical straps made of rubber, comprising four branches provided with a hole at their extremity, in which the lugs of a grid take place, said grid being set around the male hole (adaptor (2)) intended to connect the mask to the respirator tube.

In an other embodiment (FIG. 3) the shell of the buccal mask presents on each side of the mouth and along its axis, some lugs (6) on which are secured the hole of classical straps made of rubber.

Figure 10:
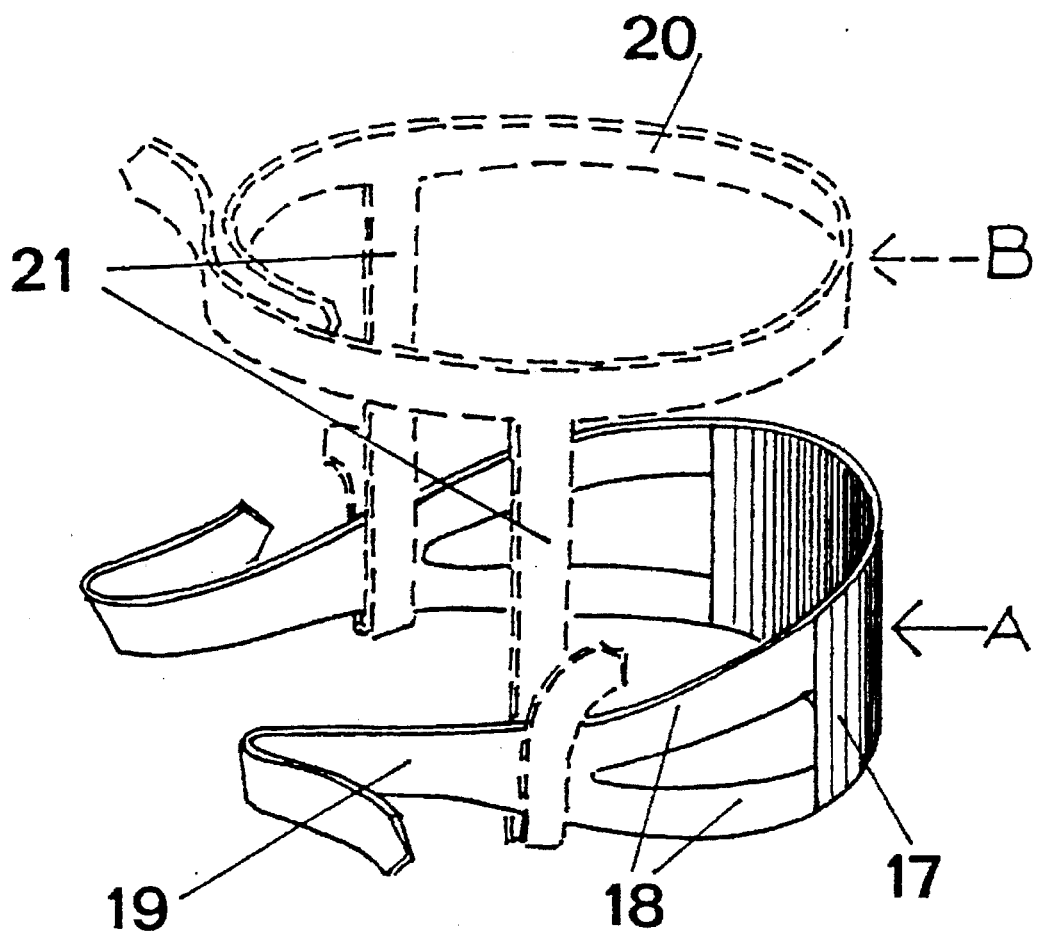

Nevertheless, specific harness is preferably used, said harness being made for buccal mask (FIG. 10, part A). It comprises an elastic rectangle (17), set on the patient's nucha where, on each side of which are inserted two straps (18) forming a V. The extremity of each V-shaped strap extends with a band (19) which passes around the anchorage points or tabs (4) of the mask's shell, and are folded back upon itself, said band being fastened by a system of hook and buckle made of tissue of the type of the well-known system sold under the Trade Mark Velcro. If necessary, in odrer to ensure the stability of the mask (agitated patient), a second part can be added to the harness (FIG. 10, partie B). It consists in an elastic strap (20) which surrounds the patient's head, and is folded back upon itself, and is fastened by a system of the Velcro type. On this head-band, two straps (21) are fixed, which go down the patient's face, between the eyes and the ears, and which join together with the harness previously described, passing round its fasteners (19) before folding back upon themself, and being fastened by a system of the Velcro type.

Figure 11:
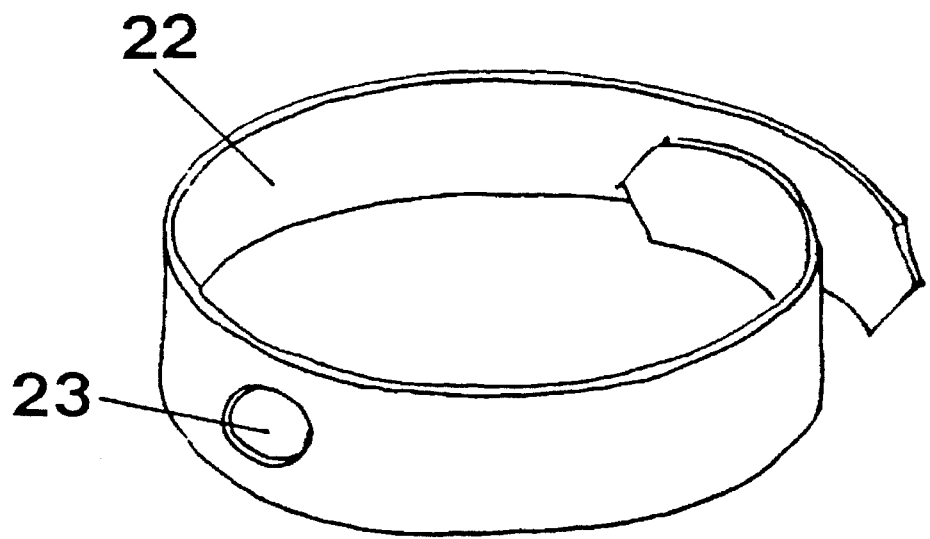

Finally, there exists another kind of fastening element (FIG. 11), which can be either used alone or used in association with the previous harness described to increase its efficiency. It consists in a band (22) made of elastic or rubber for example, with an aperture (23) through which passes the mask's adaptor (2). This band goes upon the mask, securing it on its whole length to the periphery of the patient's mouth, and then, is folded back upon itself and then fastened by a system of the Velcro type after being set on the patient's nucha.

I claim:

1. Respiratory mask used for mechanic non-invasive ventilation with positive pressure, comprising:

a mask;

said mask being exclusively buccal with no piece in the mouth and including a shell provided on its periphery with a seal which surrounds a patient's mouth and applies against an area between a nose and an upper lip, a lower lip and a chin, and against an area of right and left cheeks lying outside labial commissures of said patient.

2. Mask according to claim 1, wherein said shell has an inner volume of less than 100 ml.

3. Mask according to claim 1, wherein said shell is provided in front the patient's mouth with an adaptor intended to connect said mask to a inspiration-expiration tube of a respirator.

4. Mask according to claim 1, wherein said shell is provided on each side of the mouth and along the axis of the mouth with a tab or a lug intended to secure a fastening strap.

5. Mask according to claim 1, wherein said seal is composed of an inflated cushion which shape is such that, while ensuring air-tightness with the mouth, it obturates with its upper part the patient's nostrils in applying against them.

6. Mask according to claim 4, wherein said fastening strap is composed of an elastic rectangle set on the patient's nucha, on each side of which are inserted two straps forming a V, the extremity of each V-shape strap extending with a band passing around the anchorage points or tabs of the mask's shell, and folding back upon itself in order to be fastened by means of a system of hooks and buckles made of tissue.

7. Mask according to claim 6, wherein said fastening strap further comprises an elastic strap intended to surround the patient's head, said strap being folded back upon itself in order to be fastened by means of a system of hooks and buckles made of in tissue, and further comprising two additional straps intended to secure it with said fastening strap or harness after passing around its bands, said bands being fastened after folding back upon themself by means of a system of hooks and buckles made of tissue.

8. Mask according to claim 4, wherein said fastening strap is composed of an elastic or rubber band provided with an aperture through which passes said mask adaptor, said band extending upon the mask after being set on the patient's nucha and then being folded back upon itself in order to be fastened by means of a system of hooks and buckles made of tissue.

* * * * *